(12) United States Patent
Abril

(10) Patent No.: US 7,566,570 B2
(45) Date of Patent: Jul. 28, 2009

(54) METHOD FOR THE SEPARATION OF PHOSPHOLIPIDS FROM PHOSPHOLIPID-CONTAINING MATERIALS

(75) Inventor: Jesus Ruben Abril, Westminster, CO (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

(21) Appl. No.: 11/045,010

(22) Filed: Jan. 26, 2005

(65) Prior Publication Data

US 2005/0215803 A1 Sep. 29, 2005

Related U.S. Application Data

(60) Provisional application No. 60/539,429, filed on Jan. 26, 2004.

(51) Int. Cl.
  *G01N 33/92* (2006.01)
  *C07F 9/02* (2006.01)
(52) U.S. Cl. .......................... 436/71; 558/146
(58) Field of Classification Search ................. 560/218, 560/248; 558/70
  See application file for complete search history.

(56) References Cited

U.S. PATENT DOCUMENTS

| | | | |
|---|---|---|---|
| 4,367,178 A | 1/1983 | Heigel et al. | |
| 5,928,696 A | 7/1999 | Best et al. | |
| 6,265,593 B1 | 7/2001 | Best et al. | |
| 6,512,131 B1 | 1/2003 | Best et al. | |
| 2002/0197687 A1 | 12/2002 | Brunner et al. | |

FOREIGN PATENT DOCUMENTS

| CA | 1335054 | * | 4/1995 |
|---|---|---|---|
| EP | 0776356 B1 | | 6/1999 |
| EP | 0943675 | | 6/2003 |
| JP | 03020397 | * | 1/1991 |
| JP | 03-058994 | | 3/1991 |
| JP | 1991058994 | * | 3/1991 |
| WO | WO-01/53512 A1 | | 7/2001 |
| WO | WO-01/76385 A1 | | 10/2001 |
| WO | WO-01/76715 A2 | | 10/2001 |

OTHER PUBLICATIONS

Jul. 21, 2005 Search Report from PCT/US05/03614.
Database JPO on STN, Accession No. 1991-058994, Kamata et al. "Fractionation Process for Lipid," Patent Abstracts of Japan (CD-ROM), Unexamined Applications, Mar. 14, 1991, abstract.

* cited by examiner

*Primary Examiner*—Karl J Puttlitz
(74) *Attorney, Agent, or Firm*—Sheridan Ross P.C.

(57) ABSTRACT

Methods are disclosed for extracting and separating polar lipids, including phospholipids, from materials containing oil, polar lipid, protein, ash, and/or carbohydrate, such as egg yolks and other phospholipid-containing materials. In particular, methods for extracting phospholipids from phospholipid-containing materials through the use of an aliphatic alcohol and control of temperature are disclosed. Using these methods, phospholipids in the aqueous liquid fraction will be efficiently separated and will precipitate readily, and can be subjected to separation for improved purity.

50 Claims, 3 Drawing Sheets

METHOD FOR THE SEPARATION OF PHOSPHOLIPIDS FROM PHOSPHOLIPID-CONTAINING MATERIALS

CROSS-REFERENCE TO RELATED APPLICATION

This application claims the benefit of priority under 35 U.S.C. § 119(e) to U.S. Provisional Application Ser. No. 60/539,429, filed Jan. 26, 2004, which is incorporated herein by reference in its entirety.

FIELD OF THE INVENTION

The present invention relates to a process for extracting and separating polar lipids, including phospholipids, from materials containing oil, polar lipid, protein, ash, and/or carbohydrate.

BACKGROUND OF THE INVENTION

Examples of polar lipids include phospholipids (e.g., phosphatidyl choline, phosphatidyl ethanolamine, phosphatidyl inositol, phosphatidyl serine, phosphatidylglycerol, and diphosphatidylglycerols), cephalins, sphingolipids (sphingomyelins and glycosphingolipids), lysophospholipids and glycoglycerolipids. Phospholipids are composed of the following major structural units: fatty acids, glycerol, phosphoric acid, amino alcohols, and carbohydrates. They are generally considered to be structural lipids, playing important roles in the structure of the membranes of plants, microbes and animals. Because of their chemical structure, polar lipids exhibit a bipolar nature, exhibiting solubility or partial solubility in both polar and non-polar solvents. The term polar lipid, within the present description, is not limited to natural polar lipids but also includes chemically modified polar lipids.

One of the important characteristics of polar lipids, and especially phospholipids, is that they commonly contain polyunsaturated fatty acids (PUFAs), fatty acids with two or more unsaturated bonds. In many plant, microbial and animal systems, they are especially enriched in the highly unsaturated fatty acids (HUFAs), fatty acids with 4 or more unsaturated bonds, of the omega-3 and omega-6 series. Although these highly unsaturated fatty acids are considered unstable in triacylglycerol form, they exhibit enhanced stability when incorporated into phospholipids. A primary source of HUFA and/or PUFA-rich polar lipids is egg yolk. Several processes are used for the recovery of egg phospholipids on an industrial scale.

Previous methods to separate polar lipids, which include phospholipid-containing materials, from native biomaterials have been disclosed in WO 01/76715, "Method for the Fractionation of Oil and Polar Lipid-Containing Materials." Other disclosures include International Patent Publication No. WO 01/76385 and Canadian Patent No. 1,335,054. These disclosures teach a number of different processes regarding the separation of non-polar/neutral lipidic compounds or oils (triacylglycerides, cholesterol, pigments, hydrocarbons, etc), from polar lipidic compounds (phospholipids, cephalins, sphingomyelins, etc) by the use of water and organic soluble solvents (ethanol, isopropanol, etc.), aided by the force of centrifugation and differences in densities, combined with the degree of solubility and partition between the aqueous, organic fraction and the oil and the residual, solid fraction (insoluble proteins, ash and carbohydrates). These processes, although practical, require the use of high concentrations (greater than 50%) alcohol in some or all steps which can add costs and decrease efficiency of partitioning between neutral and polar lipids, as neutral fats are more soluble in high concentrations of alcohol. Accordingly, processes to separate phospholipids from other components still have possibilities for improvements, such as the minimization of unit operations or processing steps, as well as reduction in the cost of final production with improved yield and purity of the polar lipids.

Other processes used in the past include the use of a combination of organic solvents such as hexane, acetone, isopropanol and ethanol to extract the neutral fats using non-polar solvents from dry egg yolk, while the more polar solvents have been used to further extract the polar fractions from the yolk-extracted residue. The previous processes have several drawbacks, including the use of organic solvents (i.e. hexane and acetone) that have a higher toxicity than ethanol or isopropanol. Also, some processes require a dry matrix (egg yolk powder) to start the process, which subjects the egg to a heat treatment, lowering the quality of the starting material. This drying step also adds to the cost of the final product. In addition, the large amount of solvent needed to completely extract the oil from the matrix and subsequent polar materials is costly.

In other cases, to avoid the use of hexane or acetone, numerous processes have been proposed involving the use of supercritical fluids, especially supercritical $CO_2$. For example, U.S. Pat. No. 4,367,178 discloses the use of supercritical $CO_2$ to partially purify crude soy lecithin preparation by removing the oil from the preparation. However, supercritical fluid extraction systems are very expensive and cannot be operated continuously. Further, extraction times are long and the egg yolks or other biomaterials typically must be dried before extraction, and this increases the difficulties of stabilizing the starting dry product with antioxidants. All of these factors make the supercritical process one of the most expensive options for extracting and recovering polar-lipid material or mixtures of these materials, and although it is an elegant solution, supercritical $CO_2$ still only removes the neutral lipids from the matrix, leaving behind the polar lipids entrained with the proteins, etc., which will need subsequent extraction with a polar solvent.

Thus, there remains a need for improved processes for the extraction and separation of polar lipids from polar lipid-containing material.

SUMMARY OF THE INVENTION

The unique solution of this invention incorporates an unexpected process phenomenon of precipitation of the polar lipids once they are extracted from a phospholipid-containing material, such as a liquid egg yolk matrix. In the past, ethanol was the solvent of choice to remove polar lipids (including, for example, phospholipids) from egg yolk. However, using a concentration of an aliphatic alcohol, preferably propanol (e.g., isopropanol and/or n-propanol), and preferably performing the extraction at slightly higher than room temperature, the phospholipids form a true solution, resulting in greater extraction efficiency. The phospholipids may be easily separated from the rest of the solids (mainly proteins, carbohydrates and ash) and from the nonpolar oils (including triglycerides). The true solution of phospholipids can be cooled down to room temperature (25 C) or lower, causing the phospholipids to precipitate (i.e., become insoluble). This precipitated solid can then, again, be subjected to separation using methods such as centrifugation or filtration.

This process effectively improves and simplifies existing extraction methods, the ease of extraction, the purity of the phospholipids obtained, the ease of performing further purification of phospholipids, and allows for direct extraction of phospholipids from sources such as native liquid egg yolk. The process of phospholipid extraction follows basic principles of first producing an aqueous fraction (alcohol, water and dissolved solutes) and then preferably removing, if present, a nonpolar oil fraction and an insoluble protein fraction. The basis of this invention relies on the use of an organic solvent and a temperature of extraction and precipitation to enhance precipitation of the phospholipids. Using methods of the present invention on, for example, a phospholipid-containing material such as egg yolk, three fractions are observed after centrifugation. Upon cooling to room temperature, the phospholipids precipitate out of the aqueous fraction and are suspended in a distinct yellow band.

In accordance with one embodiment, this invention provides a method for the separation of phospholipids from a phospholipid-containing material. This method includes the steps of combining the phospholipid-containing material and a water soluble aliphatic alcohol and cooling the combination to precipitate the phospholipid. In accordance with the present invention, phospholipid-containing material may be obtained from one or more of the following: poultry eggs, enriched poultry eggs, dairy products, fish, fish eggs, genetically engineered plants, seeds, a marine microorganism selected from the group consisting of order Dinophyceae, including species *Crypthecodinium cohnii*, order Thraustochytriales, including genus *Thraustochytrium*, genus *Schizochytrium*, genus *Althornia*, genus *Aplanochytrium*, genus *Japonochytrium*, genus *Labyrinthula*, genus *Labyrithuloides*, and mixtures thereof; sweetbreads, eyes and neural tissue. In a preferred embodiment, the concentration of water soluble alcohol in the combined phospholipid-containing material and a water soluble aliphatic alcohol is between about 5% and about 50%, between about 15% and about 45%, between about 25% and about 40%, and more preferably, is about 35%. A preferred water soluble alcohol includes propanol, isopropanol, n-propanol, and mixtures thereof.

Preferably, the combining step comprises mixing the phospholipid-containing material and the water soluble aliphatic alcohol, including mechanical mixing. Mechanical mixing includes mixing in an apparatus such as a stir tank, a pump, a static mixer, a homogenizer and a shear mixer. In a preferred embodiment, the step of mixing is conducted for a period of from about 20 minutes to about 120 minutes, for a period of from about 30 minutes to about 90 minutes, and most preferably for a period of about 60 minutes. Preferably, the combining step and optional mixing steps are carried out at a temperature of extraction from about 25 C to about 75 C, from about 35 C to about 70 C, from about 55 C to about 65 C, and more preferably at about 60 C. A preferred temperature for the cooling step is from about 5 C to about 35 C, from about 10 C to about 35 C, from about 20 C to about 30 C, and more preferably about 25 C (or room temperature).

Preferably, the combined phospholipid-containing material and water soluble alcohol form at least two fractions having different densities, comprising at least two of the following: a water/aliphatic alcohol fraction enriched in phospholipids, an insoluble protein fraction, and a non-polar oil enriched fraction. Preferably, one of the fractions is a water/aliphatic alcohol fraction enriched in phospholipid containing at least about 30% phospholipid and no more than about 70% protein and nonpolar oil. In a preferred embodiment, the two fractions form by gravity separation, or are formed by centrifuging the combined phospholipid-containing material and water soluble alcohol. The two fractions may form in a batch process or in a continuous process. Preferably, the phospholipid enriched fraction is recovered (i.e. separated from the nonpolar oil enriched fraction and the protein enriched fraction) by a method including mechanical centrifugation and/or filtration.

The method includes cooling either the combination or the phospholipid enriched fraction in order to precipitate the phospholipids. In a preferred embodiment, the cooling step includes cooling the combination or the phospholipid enriched fraction to a temperature of about 5 C to about 35 C, from about 10 C to about 35 C, from about 20 C to about 30 C, and more preferably about 25 C. Preferably, the precipitated phospholipid is recovered by methods including mechanical centrifugation and/or filtration.

In one embodiment, the phospholipid-containing material has a low oil content. For example, the low-oil phospholipid-containing material may have been subjected to a de-oiling step to yield a phospholipid-enriched fraction.

In another embodiment, the present invention includes a method for the separation of phospholipids from a phospholipid-containing material, which includes providing a phospholipid-containing material from a source selected from the group consisting of poultry eggs, enriched poultry eggs, dairy products, fish, fish eggs, genetically engineered plants, seeds, a marine microorganism selected from the order Dinophyceae, a marine microorganism selected from the order Thraustochytriales, sweetbreads, eyes and neural tissue. Following steps include combining propanol and the phospholipid-containing material, at a propanol concentration of from about 15% to about 45% to form a combination at a temperature of from about 35 C to about 75 C, and then allowing the combination to separate into at least two of the following fractions: a polar lipid fraction enriched in phospholipids, a nonpolar oil enriched fraction, and an insoluble protein fraction, at a temperature of from about 35 C to about 75 C. The method further includes separating the phospholipid-enriched fraction from one or both of the other two fractions at a temperature of from about 35 C to about 75 C, followed by cooling the phospholipid-enriched fraction to a temperature of from about 5 C to about 35 C to precipitate the phospholipid and separating the precipitated phospholipid.

In another embodiment, the present invention includes a method for the separation of phospholipids from a phospholipid-containing material which includes providing a phospholipid-containing material from a source selected from the group consisting of poultry eggs or enriched poultry eggs, combining propanol (35% w/w final) and the phospholipid-containing material, wherein the combining step is carried out at a temperature at about 60 C, separating the mixture into fractions, the fractions comprising at least two of the following fractions: a phospholipid-enriched fraction, a nonpolar oil enriched fraction, and an insoluble protein fraction, at a temperature of from about 35 C to about 75 C, recovering the phospholipid-enriched fraction by centrifugation in a batch process or a continuous process at a temperature of from about 35 C to about 75 C, precipitating phospholipids from the phospholipid-enriched fraction at a temperature of about 25 C, and separating the precipitated phospholipid by centrifugation or filtration.

DETAILED DESCRIPTION

The present invention relates to a process for extracting and separating phospholipids from materials which can contain oil, polar lipid, protein, ash, and/or carbohydrate. In particular embodiments, this invention is directed to extracting phospholipids from egg yolk or other phospholipid-containing materials through the use of an aliphatic alcohol and control of temperature. With this procedure, the phospholipids in an aqueous liquid fraction will precipitate more quickly and with greater efficiency than prior art methods, allowing for greater ease of separation by methods such as centrifugation or filtration. This invention incorporates an unexpected process phenomenon of precipitation (i.e., becoming insoluble) of the polar lipids, once they are extracted from, e.g., a liquid egg yolk matrix. In the past, ethanol was the solvent of choice to remove the polar lipids (phospholipids) from egg yolk. However, the present invention involves forming a true solution of phospholipids, such as by using a concentration of an aliphatic alcohol, preferably propanol (e.g., isopropanol and/or n-propanol) and performing the extraction at slightly higher than room temperature. With the methods of the present invention, significantly better efficiency of extraction into the water/alcohol fraction is observed. The water/alcohol fraction can be easily separated from the rest of the solids (mainly proteins, carbohydrates and ash) and the nonpolar oils, such as by centrifugation. The true solution of phospholipids contained in the water/alcohol fraction can be cooled to room temperature (25 C) or lower, causing the phospholipids to precipitate out of solution. This precipitated solid can then be subjected to mechanical separation such as centrifugation or filtration.

Figure 1:
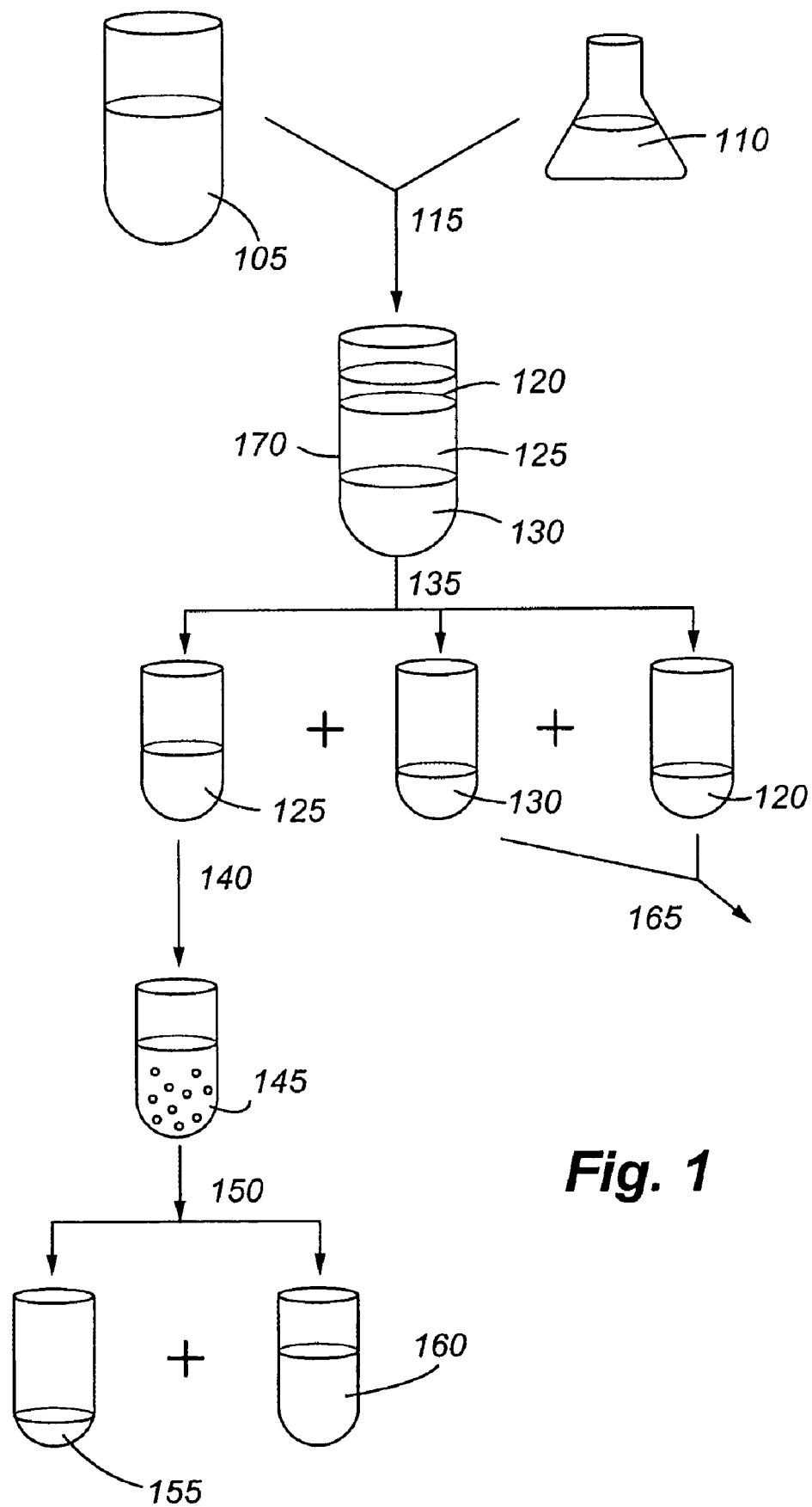
FIG. 1 is a flow diagram of a process of the present invention.

In accordance with one embodiment, this invention provides a method for the separation of phospholipids from a phospholipid-containing material. This method includes the steps of combining the phospholipid-containing material and a water soluble aliphatic alcohol to form a phospholipid-containing fraction and cooling the phospholipid-containing fraction to precipitate the phospholipids. An embodiment of this process is shown in FIG. 1.

In the first step of the process, the phospholipid-containing material 105 is combined with an aliphatic alcohol 110. In accordance with the present invention, phospholipid-containing material 105 may be obtained from one or more of the following: poultry eggs, enriched poultry eggs, dairy products, fish, fish eggs, genetically engineered plants, seeds, a marine microorganism selected from the group consisting of order Dinophyceae (including the species *Crypthecodinium cohnii*), order Thraustochytriales (including the genus *Thraustochytrium*, genus *Schizochytrium*, genus *Althornia*, genus *Aplanochytrium*, genus *Japonochytrium*, genus *Labyrinthula*, and genus *Labyrithuloides*), sweetbreads, eyes and neural tissue. Many experts argue that *Ulkenia* is not a separate genus from the genus *Thraustochytrium*. Accordingly, as used herein, the genus *Thraustochytrium* will be understood to include *Ulkenia*. Enriched poultry eggs include eggs that have been enriched by feeding the poultry an enriched diet containing ingredients comprising a phospholipid-containing material as discussed herein above, and/or eggs that have been enriched by adding ingredients such as a phospholipid-containing material as discussed herein above, to the eggs. Preferably, the eggs are in the form of yolks, with some water and protein (i.e. the white of the egg) already removed. Particularly preferred for the present invention are poultry eggs and enriched poultry eggs. Preferred phospholipids contain PUFAs of the omega-3 and omega-6 series, including docosahexaenoic acid (DHA), docosapentaenoic acid (DPA) and/or arachidonic acid (ARA).

The phospholipid-containing materials 105 can be treated prior to use in the present invention to release the lipids. For example, the phospholipid-containing materials can be treated by lysing, rupturing, or permeabilizing cells, or grinding or comminuting. Selection of suitable treatment will depend on the nature of the material and whether any particular treatment is needed for making lipids available in the present process. Such treatments are known to those skilled in the art.

A preferred aliphatic alcohol 110 for combination with a phospholipid-containing material is an alcohol with 3 or more carbons that is miscible in water at the desired alcohol concentration. In a preferred embodiment, the water soluble aliphatic alcohol 110 is propanol, and includes isopropanol, n-propanol and mixtures thereof. The water soluble aliphatic alcohol 110 is used at a concentration that is capable of first extracting at least some of the polar lipids into a water/alcohol fraction and then precipitating the polar lipid in a subsequent cooling step. Without being bound by theory, the inventors believe that longer chain aliphatic alcohols disrupt the lipid protein structure of many phospholipid-containing materials better than shorter chains such as ethanol and methanol. However, the ability of long chain aliphatic alcohols to disrupt the lipid protein structure must be balanced by the decreasing water solubility (or miscibility in water) as the chain lengths grow longer. Accordingly, longer chain alcohols like C4 (butanol and its isomers), C5 (pentanol and its isomers) and C6 (hexanol and its isomers) may be used in the present invention, but have less miscibility in water than isopropanol. Amounts of each alcohol to use will be used taking into account both increasing disruption capacity with decreasing water solubility as the chain length increases. Unless otherwise specified, reference to water soluble aliphatic alcohol includes both single aliphatic alcohols and mixtures of two or more aliphatic alcohols. In a preferred embodiment, the concentration of the water soluble aliphatic alcohol in the combination will typically range from about 5% to about 50% (w/w), wherein the lower end of the range can be about 5%, about 10%, about 15%, about 20%, about 25%, or about 30%, and the upper end of the range can be about 50%, about 45%, or about 40%. In a preferred embodiment, the concentration is about 35%.

In a particular embodiment, the step of combining can further include the step of adding water to the other components. A sufficient volume of water is added to obtain adequate transfer of and partitioning of phospholipids between the phases or fractions and allow the combination to reach the desired final concentration of aliphatic alcohol. For example, egg yolks typically have approximately 50% solids and 50% moisture, and the percent of solids and moisture will vary between batches. A sufficient amount of water can be added, taking into account the moisture in the particular batch of egg yolk used, to ensure that the desired final aliphatic alcohol concentration is achieved. As discussed herein above, the aliphatic alcohol concentrations may range from about 5% to about 50%.

The combining step 115 may be conducted in any manner described and known in the art in which two materials are introduced to each other. Preferred methods for combining include mechanical mixing. A preferred method with which to accomplish mechanical mixing is in an apparatus such as, for example, a stir tank, a pump, a static mixer, a homogenizer or a shear mixer. Typically, the phospholipid-containing materials and aliphatic alcohol are mixed for a time sufficient to make a homogeneous combination. A preferred time for which to conduct the mixing is for a period of from about 20 minutes to about 120 minutes, from about 30 minutes to about 90 minutes, and preferably, for a period of about 60 minutes.

During the combining step 115, the combined phospholipid-containing material 105 and water soluble alcohol 110 can preferably be maintained at a temperature at which the phospholipids become solubilized. Suitable temperatures can be determined for each type of material and each type of alcohol used. Preferably, the phospholipid-containing material and water soluble alcohol are maintained at a temperature of from about 35 C to about 70 C, about 55 C to about 65 C, and more preferably at about 60 C during the combining step (prior to the cooling step). Preferably, the combination is maintained at this temperature during any subsequent steps up to but not including the cooling step.

The combined phospholipid-containing material and water soluble aliphatic alcohol can constitute the phospholipids-containing fraction. Alternatively, the combined phospholipid-containing material and water soluble aliphatic alcohol can form the phospholipid-containing fraction and at least one other fraction, wherein the fractions have different densities. The phospholipid-containing fraction is typically a water/aliphatic alcohol fraction 125 enriched in phospholipids. In a preferred embodiment, the phospholipid-containing fraction contains at least about 30% by weight of phospholipids. Such a fraction would have less than about 70% by weight protein and nonpolar oil. The at least one other fraction can include a nonpolar oil-enriched fraction 120 and/or an insoluble protein fraction 130. Preferably, these fractions are separated from each other 135 by techniques known in the art referring to their different densities, including mechanical centrifugation, filtration and combinations thereof. In one embodiment, the fractions form by gravity separation. In one embodiment, the separation 135 of the fractions is accomplished by centrifuging the combined phospholipid-containing material and water soluble alcohol, yielding a separated phospholipid enriched fraction 125. Separated nonpolar oil enriched fraction 120 and separated insoluble protein fraction 130 can be further processed 165 or discarded as desired. For the phospholipid-enriched fraction 125, further processing can be performed as desired or necessary. For example, counter-current washing/centrifugation or cross-current washing/separation of the phospholipid-enriched fraction can be employed to improve the purity of the fraction and the economics of the overall process, batch or continuous.

In some embodiments, the phospholipid-containing material 105 has a low oil content, for example the phospholipid-containing material can either intrinsically have a low oil content or can be de-oiled. To accomplish de-oiling, the material 105 can be treated using methods either disclosed in the present invention or disclosed previously by others. For example, de-oiling with supercritical carbon dioxide will result in removal of nonpolar oil but not phospholipid.

A particularly preferred embodiment includes a propanol as the water soluble aliphatic alcohol 110. Use of propanol and longer chain alcohols can result in greater efficiency of the process, i.e. extraction and/or partition of phospholipids into the water/alcohol fraction 125 such that a greater quantity of phospholipid appears in fraction 125. Efficiency can be measured by determining the percentage by weight of phospholipids (on a dry matter basis) extracted from the source relative to all of the constituents in fraction 125. In a preferred embodiment, the efficiency of the process can range from about 30% to about 90%, and more particularly is, on the lower end of the range, about 30%, about 40%, about 45%, about 50%, about 55%, about 60%, and on the upper end of the range is about 65%, about 70%, about 75%, about 80%, and about 90%.

Use of propanol and longer chain alcohols can also result in greater yield of the process, i.e. extraction and/or partition of phospholipids into the water/alcohol fraction 125 such that a greater quantity of phospholipid appears in fraction 125. Yield can be measured by determining the percentage by weight of phospholipids (on a dry matter basis) extracted from the source relative to the total amount of phospholipids initially in the source 105. In a preferred embodiment, the yield of the process can range from about 30% to about 90%, and more particularly is, on the lower end of the range, about 30%, about 40%, about 45%, about 50%, about 55%, about 60%, and on the upper end of the range is about 65%, about 70%, about 75%, about 80%, and about 90%.

Because of the simplicity of the equipment required in the process, the entire process can easily be conducted under a reduced-oxygen atmosphere (e.g., nitrogen), protecting any PUFAs in the polar lipids from oxidation. For example, a gas tight decanter can be used to separate a protein fraction. A suitable decanter is model CA 226-28 Gas Tight, available from Westfalia Separator Industry GmbH of Oelde, Germany, which is capable of continuous separation of protein from suspensions with a high protein solids content in a centrifugal field. A gas tight separator useful for separating polar lipids from oil is model SC 6-06-576 Gas Tight, available from Westfalia Separator Industry GmbH of Oelde, Germany.

The step of cooling the phospholipid-containing fraction can include either cooling the combination 170 comprising a phospholipid-enriched fraction 125 and/or cooling 140 a separated phospholipid-enriched fraction 125 to precipitate phospholipids out of solution, as shown in FIG. 1. Suitable cooling temperatures may be selected based on the characteristics of the particular phospholipid-containing material and the particular water soluble aliphatic alcohol being used, with temperatures ranging from about 5 C to about 35 C. On the lower end of the range, preferred temperatures include temperatures of at least about 5 C, at least about 10 C, at least about 15 C, and at least about 20 C. On the upper range, preferred temperatures include temperatures of at most about 30 C, or at most about 35 C. A preferred temperature is about 25 C. The cooling step is conducted for a time sufficient to achieve a desired degree of precipitation, with a shorter length of time (less than about 30 minutes) preferred. Preferably, the precipitated phospholipids 155, a solid, are separated 150 from the cooled aliphatic alcohol/water fraction 145, a liquid, to produce an alcohol/water fraction 160 by any suitable solid/liquid separation method known in the art, including mechanical centrifugation, filtration and combinations thereof.

A preferred embodiment of the present invention is a method for the separation of phospholipids from a phospholipid-containing material. The method includes combining propanol and a phospholipid-containing material. The phospholipid-containing material is from a source selected from poultry eggs, enriched poultry eggs, microorganisms of the genus *Thraustochytrium*, microorganisms of the genus *Schizochytrium*, microorganisms of the species *Crypthecodinium cohnii* and mixtures thereof. The propanol and the phospholipid-containing material are combined at a temperature of from about 35 C to about 75 C. The combination is allowed to form a water/propanol fraction enriched in phospholipids at a temperature of from about 35 C to about 75 C. The phospholipid-enriched fraction is cooled to a temperature of from about 5 C to about 35 C to precipitate phospholipids from the fraction. The precipitated phospholipids are then separated.

A further preferred embodiment of the present invention is a method for the separation of phospholipids from a phospholipid-containing material. This method includes combining propanol and a phospholipid-containing material. The phospholipid-containing material is from a source selected from the group consisting of poultry eggs and enriched poultry eggs. The propanol and phospholipid-containing material are combined at a temperature of from about 35 C to about 75 C. The combination is separated into a phospholipid-enriched fraction and a protein fraction at a temperature of from about 35 C to about 75 C. The method further includes recovering the phospholipid-enriched fraction by centrifugation in a batch process or a continuous process at a temperature of from about 35 C to about 75 C. Phospholipids are precipitated from the phospholipid-enriched fraction at a temperature of about 25 C. The precipitated phospholipids are separated by centrifugation or filtration.

The present invention, in various embodiments, includes components, methods, processes, systems, and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease, and/or reducing cost of implementation.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

EXAMPLES

Example 1

This Example describes testing of egg yolk with processes of the present invention comparing isopropanol and ethanol.

An exemplary process is as follows. Egg yolk (100 g) was obtained. Water was added to the yolk, accounting for natural water in the egg, and either ethanol was added to a final concentration of 33.6% by weight or isopropanol was added at 35% by weight. The procedure for addition to the isopropanol was as follows: in 100 g egg yolk, 48.79 g were solids. 60.27 g of 85% isopropanol and 34.89 g water were added to the 100 g egg yolk (48.79 g solids and 51.21 g water). Total weight of the mixture after additions of alcohol and water was 195.16 g. All other samples were prepared in this same way. Samples were malaxed at 60 C for 1 hour, and centrifuged at 4,500 RPM for 6 minutes. The ethanol sample was left to stand at refrigerator temperature at 12 hours, while the isopropanol sample was left at room temperature for 4 hours.

Figure 2:
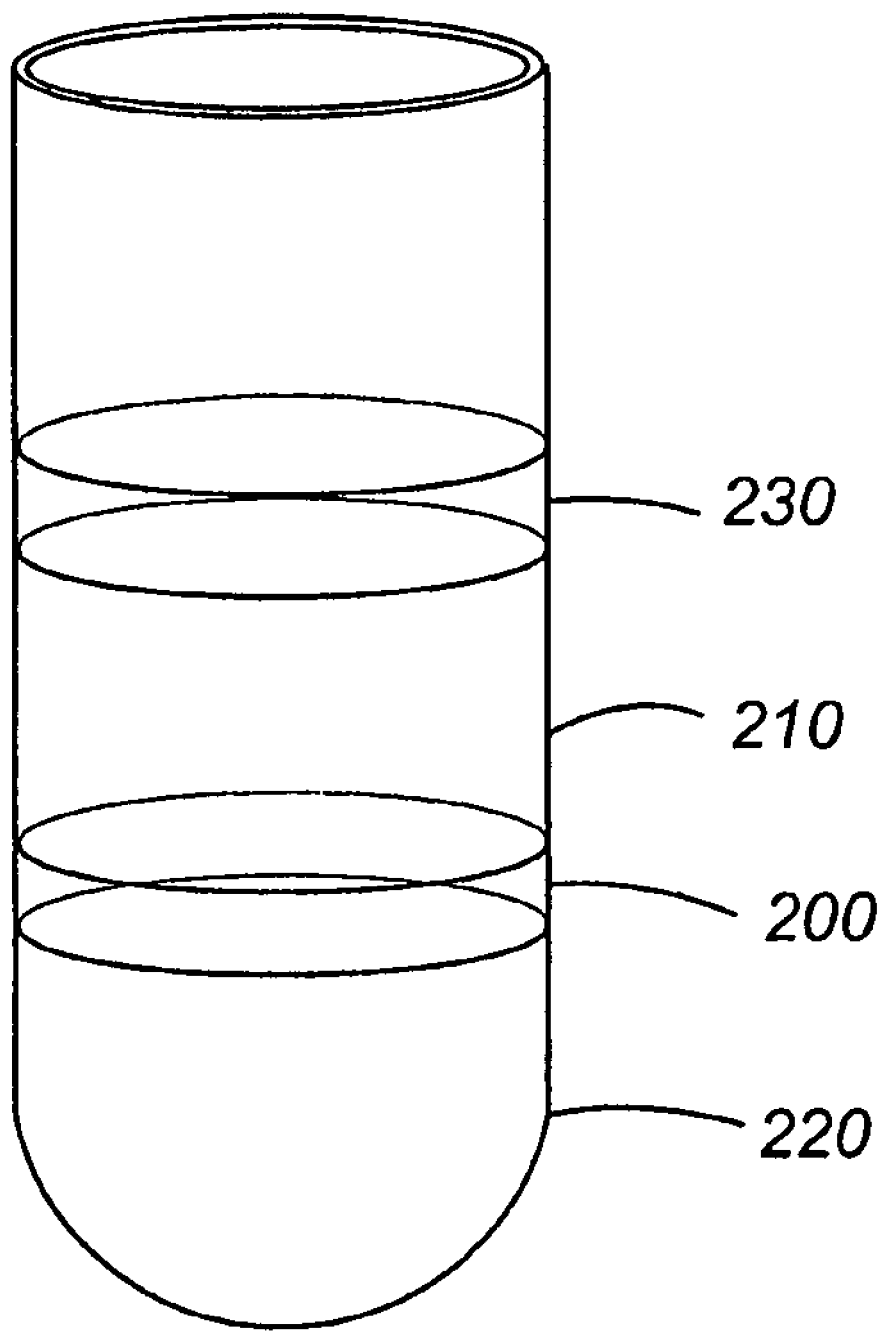
FIG. 2 depicts a centrifuge tube containing egg yolk treated by a method of the present invention, resulting in a mixture containing several fractions, including a nonpolar oil fraction, a water/alcohol (intermediate) fraction, a precipitated phospholipid layer, and a protein pellet.

FIG. 2 depicts a centrifuge tube containing egg yolk treated by methods of the present invention, resulting in a mixture containing several fractions, including a nonpolar oil fraction, a water/alcohol (intermediate) fraction, a precipitated phospholipid layer, and a protein pellet. More specifically, FIG. 2 depicts a distinct band of precipitated phospholipid 200 formed underneath an intermediate fraction 210, containing the water/alcohol fraction. Underneath the intermediate fraction 210, a protein pellet 220 formed. The very top layer was egg oil 230 which included triglycerides and other nonpolar lipids. It was noted that, when using isopropanol, the precipitated phospholipid 200 appeared when the intermediate fraction is cooled to room temperature.

Figure 3:
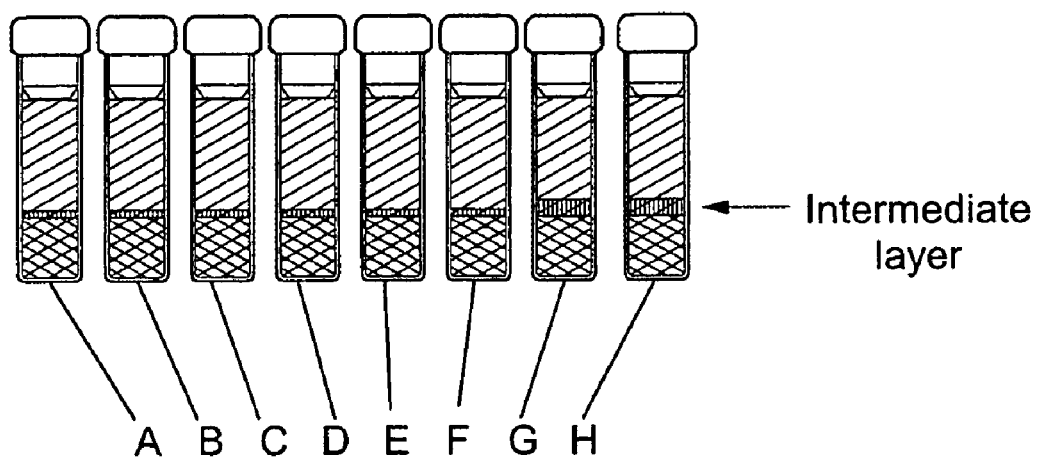
FIG. 3 depicts centrifuge tubes containing different fractions resulting from treatment of egg yolk with methods of the present invention, comparing use of isopropanol and use of ethanol.

FIG. 3 shows a sequence of extraction tubes showing the formation of the phospholipids-containing intermediate layer. Tubes A and B are ethanol extracted, 35%, 4 hours room temperature, with fresh and pasteurized egg yolk respectively; tubes C and D are ethanol extracted, 35%, 12 hours refrigeration temperature, with fresh and pasteurized egg yolk respectively; tubes E and F are ethanol extracted, 45%, 4 hours room temperature, with fresh and pasteurized egg yolk respectively; and tubes G and H are isopropanol extracted, 4 hours room temperature, with fresh and pasteurized egg yolk respectively. The results show the formation of the intermediate layer in all samples, with best results with isopropanol.

Figure 4:
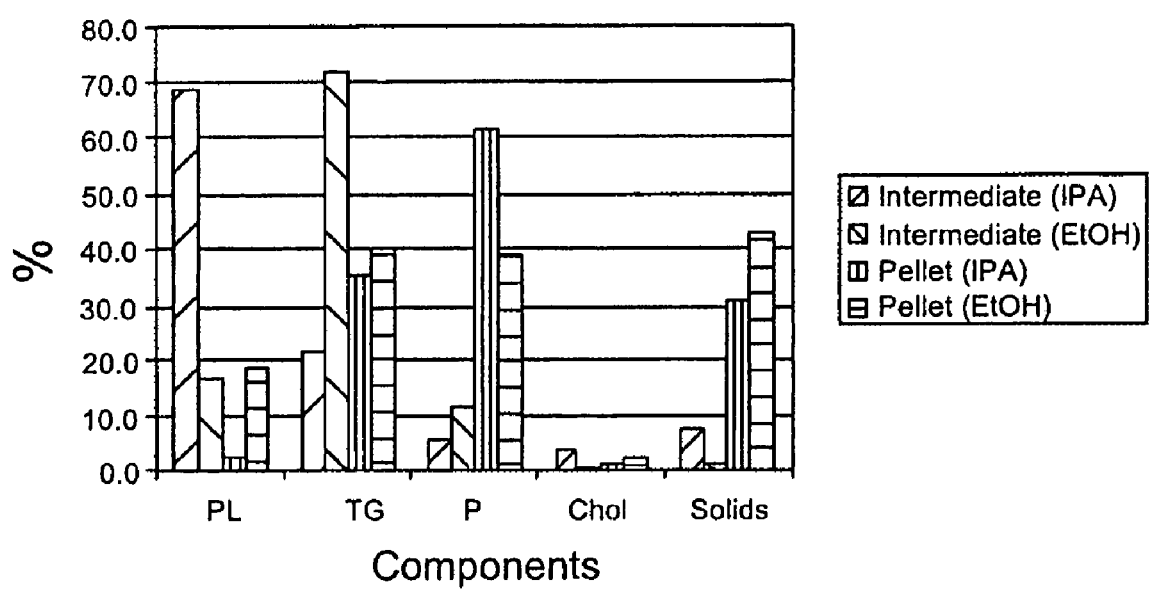
FIG. 4 is a graph showing the phospholipid content, triglyceride content, protein content, cholesterol content, and solid content of both intermediate (water/alcohol) fractions and pellet fractions from egg yolks treated with either ethanol or isopropanol.

FIG. 4 shows the composition of the phospholipid fraction obtained from the ethanol or isopropanol intermediate phases. The "solids" bars shows the amount of solids contained in the isopropanol intermediate phase, the ethanol intermediate phase, the isopropanol pellet, and the ethanol pellet. For the ethanol intermediate phase, the solids content is fairly low (less than 2%), whereas in the isopropanol intermediate phase, the solids content is approximately 8%. The solids from each of these phases were then analyzed for phospholipids (PL), triacylglyceride (TG), protein (P), and cholesterol (Chol). The percentage of PL in the solid is quite high in the isopropanol intermediate phase (almost 70%) and lower in the ethanol intermediate phase (approximately 17%). The percentage of PL in the solid for the pellet (which is discarded in the process) is quite low for the isopropanol pellet (approximately 3%) but more in the ethanol pellet (almost 20%). For TG, the TG percentage in the solid is lowest in the isopropanol intermediate phase at just over 20%, much higher in the ethanol intermediate phase at over 70%, and approximately 35% and 40% in the isopropanol pellet and the ethanol pellet, respectively. The amounts of protein in the isopropanol and ethanol intermediate solids are approximately 5% and 11% respectively. Overall, an isopropanol extracted intermediate contains enhanced amount of phospholipid and a reduced amount of triacylglyceride compared to an ethanol extracted intermediate.

Example 2

This Example describes an embodiment of the method of the present invention using isopropanol as the water soluble aliphatic alcohol. Isopropanol and water were added and the combination was placed to heat to 55 C in a mixing chamber and the pump started. The pump was a high speed recirculating pump manufactured by Westfalia Separator Industry GmbH (Oelde, Germany). 20 kg of commercial pasteurized egg yolk previously heated to 55 C in a hot water bath was then added to the mixing chamber. The final mixture achieved an alcohol concentration of 39.47% (w/w). Mixing was continued for 1.5 hours, which was accomplished by a high speed recirculating pump with an external marine-type impeller/agitator added to the system to aid in the mixing.

After 1.5 hours, the mixture was diverted to a manual discharge disk centrifuge (Westfalia Separator Industry) and spun at approximately 9500 rpm. Flow of fluid was manually controlled and discharges were done periodically when it was determined that the bowl was close to being full. The discharges contained egg protein. This egg protein was not completely de-oiled. The centrifuge was run on a one fraction mode, and therefore the light fraction (the egg oil comprising triglycerides, approximately 9 kg) and the heavy fraction (water/alcohol intermediate fraction, approximately 25 kg) were collected together. The whole volume was processed in about 2 hours.

The liquid fraction was collected, re-heated to 55-60 C, and mixed with the pump and agitator. Then the flow was again diverted to the centrifuge to remove more of the solids (protein). This time the centrifuge was operated in two stage mode, separating the oil from the alcohol/water intermediate fraction. This process took one hour, and after this the clarified liquid (intermediate fraction minus oil fraction) was reprocessed again for a third time. The final intermediate fraction was clear and yellow in color.

The intermediate fraction was left to cool down to room temperature allowing polar lipids to precipitate. The material containing the precipitated phospholipids was passed through the centrifuge again, and the discharge was collected which represented the polar lipids including phospholipids. A total of 9 kg solids were collected. The solids content of the cooled intermediate fraction was about 17%.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

I claim:

1. A method for the separation of phospholipids from a phospholipid-containing material, comprising:
   a. combining the phospholipid-containing material and a water soluble aliphatic alcohol to form a phospholipid-containing fraction;
   b. cooling the phospholipid-containing fraction to precipitate the phospholipids.

2. The method of claim 1, wherein the phospholipid-containing material is obtained from a source selected from the group consisting of a marine microorganism of the genus *Thraustochytrium*, genus *Schizochytrium*, genus *Althornia*, genus *Aplanochytrium*, genus *Japonochytrium*, genus *Labyrinthula*, genus *Labyrithuloides*, species *Crypthecodinium cohnii* and mixtures thereof.

3. The method of claim 1, wherein the concentration of the water soluble aliphatic alcohol in the combination is from about 5% to about 50% (w/w).

4. The method of claim 1, wherein the concentration of the water soluble aliphatic alcohol in the combination is from about 15% to about 45% (w/w).

5. The method of claim 1, wherein the concentration of the water soluble aliphatic alcohol in the combination is from about 25% to about 40% (w/w).

6. The method of claim 1, wherein the concentration of the water soluble aliphatic alcohol in the combination is about 35% (w/w).

7. The method of claim 1, wherein the water soluble aliphatic alcohol is propanol.

8. The method of claim 7, wherein the propanol is selected from the group consisting of isopropanol, n-propanol and mixtures thereof.

9. The method of claim 1, wherein the step of combining comprises mixing the phospholipid-containing material and the water soluble aliphatic alcohol.

10. The method of claim 9, wherein the step of mixing comprises mechanical mixing.

11. The method of claim 10, wherein the step of mixing comprises mixing the phospholipid-containing material and the water soluble aliphatic alcohol in an apparatus selected from the group consisting of a stir tank, a pump, a static mixer, a homogenizer and a shear mixer.

12. The method of claim 10, wherein the step of mixing is conducted for a period of from about 20 minutes to about 120 minutes.

13. The method of claim 10, wherein the step of mixing is conducted for a period of from about 30 minutes to about 90 minutes.

14. The method of claim 10, wherein the step of mixing is conducted for a period of about 60 minutes.

15. The method of claim 1, wherein the combined phospholipid-containing material and water soluble aliphatic alcohol form the phospholipid-containing fraction and at least one other fraction, wherein the fractions have different densities.

16. The method of claim 15, wherein the two fractions form by gravity separation.

17. The method of claim 15, further comprising centrifuging the combined phospholipid-containing material and water soluble alcohol to form the two fractions.

18. The method of claim 15, wherein the two fractions form in a batch process.

19. The method of claim 15, wherein the two fractions form in a continuous process.

20. The method of claim 15, wherein the phospholipid-enriched fraction is cooled to precipitate the phospholipids.

21. The method of claim 15, wherein the at least one other fraction comprises either a nonpolar oil enriched fraction or an insoluble protein fraction.

22. The method of claim 15, wherein the phospholipid-containing fraction contains at least about 30% phospholipid.

23. The method of claim 22, further comprising recovering the phospholipid-containing fraction by a method selected from the group consisting of mechanical centrifugation, filtration and combinations thereof.

24. The method of claim 1, wherein the combined phospholipid-containing material and water soluble alcohol are maintained at a temperature of about 35 C to about 70 C during the combining step.

25. The method of claim 1, wherein the combined phospholipid-containing material and water soluble alcohol are maintained at a temperature of about 55 C to about 65 C during the combining step.

26. The method of claim 1, wherein the combined phospholipid-containing material and water soluble alcohol are maintained at a temperature of about 60 C during the combining step.

27. The method of claim 1, wherein the cooling step comprises cooling the combination to a temperature of from about 5 C to about 35 C.

28. The method of claim 1, wherein cooling step comprises cooling the combination to a temperature of from about 10 C to about 35 C.

29. The method of claim 1, wherein the cooling step comprises cooling the combination to a temperature of from about 20 C to about 30 C.

30. The method of claim 1, wherein the cooling step comprises cooling the combination to a temperature of about 25 C.

31. The method of claim 1, further comprising separating the precipitated phospholipids.

32. The method of claim 31, wherein the separating step is selected from the group consisting of mechanical centrifugation, filtration and combinations thereof.

33. The method of claim 1, wherein the phospholipid-containing material has a nonpolar oil content of no more than 70%.

34. The method of claim 33, wherein the phospholipid-containing material has been deoiled to remove nonpolar oils.

35. A method for the separation of phospholipids from a phospholipid-containing material comprising:
(a) combining propanol and a phospholipid-containing material from a source selected from the group consisting of poultry eggs, enriched poultry eggs, microorganisms of the genus *Thraustochytrium*, microorganisms of the genus *Schizochytrium*, microorganisms of the species *Crypthecodinium cohnii* and mixtures thereof at a temperature of from about 35 C to about 75 C;
(b) allowing the combination to form a water/propanol fraction enriched in phospholipids at a temperature of from about 35 C to about 75 C;
(c) cooling the phospholipid-enriched fraction to a temperature of from about 5 C to about 35 C to precipitate the phospholipids; and
(d) separating the precipitated phospholipids.

36. The method of claim 35, wherein the step of combining further comprises mixing the phospholipid-containing material and the propanol in an apparatus selected from the group consisting of a stir tank, a pump, a static mixer, a homogenizer, and a shear mixer.

37. The method of claim 36, wherein the mixing step is carried out for a period of about 60 minutes.

38. The method of claim 35, wherein the combination is maintained at a temperature of about 60 C during the allowing step.

39. The method of claim 35, wherein the cooling step comprises cooling the combination to a temperature of about 25 C.

40. The method of claim 35, wherein the step of separating comprises centrifugation.

41. The method of claim 35, wherein the fraction forms in a batch process.

42. The method of claim 35, wherein the fraction forms in a continuous process.

43. The method of claim 35, wherein the phospholipid-containing material has a low nonpolar oil content.

44. The method of claim 43, wherein the phospholipid-containing material has been deoiled to remove nonpolar oils.

45. A method for the separation of phospholipids from a phospholipid-containing material comprising:
(a) combining propanol and a phospholipid-containing material from a source selected from the group consisting of poultry eggs and enriched poultry eggs at a temperature of about 60 C;
(b) separating the combination into a phospholipid-enriched fraction and a protein fraction at a temperature of from about 35 C to about 75 C;
(c) recovering the phospholipid-enriched fraction by centrifugation in a batch process or a continuous process, at a temperature of from about 35 C to about 75 C;
(d) precipitating phospholipid from the phospholipid-enriched fraction at a temperature of about 25 C; and
(e) separating the precipitated phospholipid by centrifugation or filtration.

46. The method of claim 45, wherein the phospholipid-containing material has been de-oiled.

47. The method of claim 46, wherein the phospholipid-containing material has been deoiled prior to step (a).

48. A method for the separation of phospholipids from a phospholipid-containing material, comprising:
a. combining the phospholipid-containing material and a water soluble aliphatic alcohol to form a phospholipid-containing fraction, wherein the concentration of the water soluble aliphatic alcohol in the combination is from about 5% to about 50% (w/w);
b. cooling the phospholipid-containing fraction to precipitate the phospholipids.

49. A method for the separation of phospholipids from a phospholipid-containing material, comprising:
a. combining the phospholipid-containing material and a water soluble aliphatic alcohol to form a phospholipid-containing fraction and at least one other fraction, wherein the fractions have different densities;
b. cooling the phospholipid-containing fraction to precipitate the phospholipids.

50. A method for the separation of phospholipids from a phospholipid-containing material, comprising:
a. combining the phospholipid-containing material and isopropanol to form a phospholipid-containing fraction;
b. cooling the phospholipid-containing fraction to precipitate the phospholipids.

* * * * *